United States Patent [19]

Okada et al.

[11] Patent Number: 4,897,105

[45] Date of Patent: Jan. 30, 1990

[54] HERBICIDAL COMPOUNDS, THEIR PRODUCTION AND USE

[75] Inventors: Yoshiyuki Okada, Suita; Isao Aoki, Kawanishi; Nobuyuki Okajima, Osaka; Takashi Kuragano, Takarazuka, all of Japan

[73] Assignee: Takeda Chemical Industries, Ltd., Osaka, Japan

[21] Appl. No.: 28,692

[22] Filed: Mar. 20, 1987

[30] Foreign Application Priority Data

Mar. 25, 1986 [JP] Japan .................................. 61-67821

[51] Int. Cl.$^4$ ..................... A01N 43/90; C07D 513/04
[52] U.S. Cl. ......................................... 71/90; 544/255; 544/63; 544/72; 544/82; 544/80; 544/96; 544/98; 544/117
[58] Field of Search ...................... 71/90; 544/255, 63, 544/72, 82, 80, 96, 98, 117

[56] References Cited

U.S. PATENT DOCUMENTS 3,660,405  5/1972  Berger et al. ............... 544/255
3,726,891  4/1973  Pilgram et al. .............. 260/306.7
4,098,888  7/1978  Ochiai et al. ................. 544/21
4,355,160 10/1982  Ochiai et al. ................. 544/21
4,411,690 10/1983  Tseng .......................... 544/255

FOREIGN PATENT DOCUMENTS 58476  8/1982  European Pat. Off. .
0150974  8/1985  European Pat. Off. .

*Primary Examiner*—John M. Ford
*Attorney, Agent, or Firm*—Wenderoth, Lind & Ponack

[57] ABSTRACT

A compound of the general formula

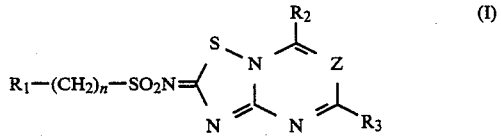

wherein $R_1$ is a phenyl group which may be substituted, $R_2$ and $R_3$ respectively are a lower alkyl or lower alkoxy group, Z is CH or N and n is 0 or 1, or a salt thereof which is useful as a herbicide.

15 Claims, No Drawings

HERBICIDAL COMPOUNDS, THEIR PRODUCTION AND USE

The present invention relates to herbicidal compounds, their production and use. More particularly, the herbicidal compounds of the invention have the following general formula:

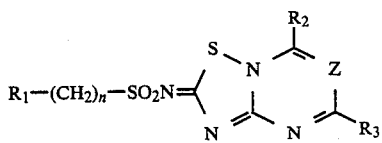

wherein $R_1$ is a phenyl group which may be substituted $R_2$ and $R_3$ respectively are a lower alkyl or lower alkoxy group, Z is CH or N and n is 0 or 1.

It should be noted that the compounds represented by the formula (I) include their salts as explained below in detail. This is applied throughout the specification.

The compounds of the general formula (I) [hereinafter, sometimes abbreviated as the compound (I)] according to this invention have an excellent herbicidal effect on paddy weeds and field weeds and no substantial damage on crops such as rice, wheat, barley, corn, soybean, etc., and can be used as an excellent selective herbicide in paddy and field. Hitherto, various compounds possessing herbicidal activity have been reported. For example, EP-A-58476 discloses the compounds represented by the general formula:

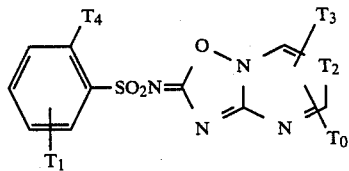

wherein is $T_0$ is F, Cl or the like, $T_1$ is hydrogen, F or the like, $T_2$ is CH or N; $T_3$ is methyl, methoxy or the like and $T_4$ is $C_{1-4}$alkyl, $C_{1-4}$alkoxy or the like. The condensed heterocyclic group to be combined with the phenylsulfonylimino group in the above mentioned compounds is a condensed ring with an oxadiazole ring, which is structurally different from the condensed ring with a thiadiazole ring in the compound (I) of the present invention. Furthermore, the above mentioned compounds can not be satisfactorily used as selective herbicide, because they exhibit damage on crops such as rice, wheat or barley. The process for production disclosed in said reference is quite different from that of the present invention and is rather complicated, the yield being relatively low.

Hitherto, many compounds have been used as herbicides. They however, are still not satisfactory in respect of the herbicidal effect against weeds, damage on crops, toxicity to mammals, fishes and shellfishes, environmental pollution and so on, and a selective herbicide improved further in these respects desired.

The inventors of this invention have made investigation after investigation with a view to developing selective herbicides having excellent herbicidal activity and substantially no damage on crops, and found that the compounds of the above-mentioned general formula (I) and their salts have a strong herbicidal activity and a remarkably reduced damage on crops such as rice, wheat, barley, corn, soybean and the like, and accordingly exhibit a highly selective herbicidal effect. On the basis of such findings, the inventors have made various further investigations and completed the present invention.

According to the invention, it provides (1) a compound of the general formula (I), (2) a process for producing a compound of the general formula (I) which comprises ring closing a compound of the general formula:

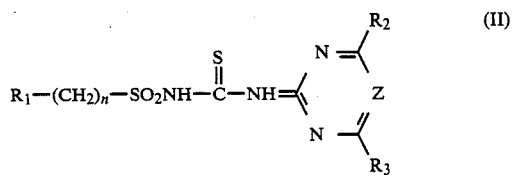

wherein the symbols have the same meanings as described above, and (3) a herbicidal composition comprising a compound of the general formula (I) as the active ingredient.

In the above general formulae, the phenyl group which may be substituted as the symbol $R_1$ means a phenyl group which may be substituted by 1 to 5 (preferably 1 to 3) the optional substituents at the optional position(s).

Preferred examples of the substituents on the phenyl group include a lower alkyl, lower alkenyl, lower alkynyl, lower alkoxy, aryl, aryloxy, aralkyl, aralkyloxy, acyl, acyloxy, acylamino, carbamoyl, thiocarbamoyl, carbamoyloxy sulfamoyl, sulfamoyloxy, halogen, carboxy, hydroxy, mercapto, lower alkylamino, arylamino, aralkylamino, nitro, cyano, or a group of the formula or

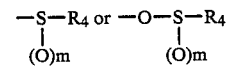

($R_4$ is an organic residue and m is 0, 1 or 2). The lower alkyl group includes a straight chain, branched chain or cyclic alkyl group containing 1 to 6 carbon atoms, such as methyl, ethyl, n-propyl, isopropyl, n-butyl, isobutyl, secbutyl, tert-butyl, n-pentyl, sec-pentyl, isopentyl, neopentyl, cyclopentyl, n-hexyl, isohexyl or cyclohexyl. The lower alkenyl group means a straight chain, branched chain or cyclic alkenyl group containing 3 to 6 carbon atoms, such as allyl, isopropenyl, 1-butenyl, 2-pentenyl, 2-hexenyl, cyclopentenyl, cyclopentadienyl or cyclohexenyl. The lower alkynyl group includes an alkynyl group containing 3 to 6 carbon atoms, such as propargyl, 2-butynyl, 3-butynyl, 3-pentyl or 3 hexynyl. The lower alkoxy- group means a straight chain, branched chain or cyclic alkoxy group containing 1 to 6 carbon atom, such as methoxy, ethoxy, n-propoxy, isopropoxy, n-butoxy, isobutoxy, sec-butoxy, tertbutoxy, n-pentyloxy, n-hexyloxy, cyclopropyloxy, cyclopentyloxy or cyclohexyloxy. The aryl group includes an aryl group containing 6 to 14 carbon atoms, such as phenyl, naphthyl or biphenylyl. The aryloxy means an aryloxy group containing 6 to 14 carbon atoms, such as phenoxy or naphthyloxy. The aralkyl group means an aralkyl group containing 7 to 19 carbon atoms, such as benzyl, phenethyl, phenylpropyl or trityl. The aralkyloxy means an aralkyloxy group containing 7 to 19 carbon atoms such as benzyloxy, phenethyloxy, phenylpropyloxy or trityloxy. The acyl group means an acyl group derived from an organic carboxylic acid, such as a lower alkylcarbonyl, lower alkenylcarbonyl, arylcarbonyl, aralkylcarbonyl, lower alkoxycarbonyl, aryloxycarbonyl, aralkyloxycarbonyl or lower alkoxycarbonyl-carbonyl group (here, the lower alkyl, lower alkenyl, aryl, lower alkoxy, aralkyl, aryl in the aryloxy, and aralkyl in the aralkyloxy have the same meanings as defined above), or a heterocyclic oxycarbonyl or heterocyclic carbonyl group here the heterocyclic group ray be a 5 or 6 membered heterocyclic group containing at least one, preferably one to four, of sulfur (which may be oxidized), oxygen or nitrogen which ray be oxidized), such as thienyl, benzothienyl, pyrrolyl, oxazolyl, piperazinyl, thiazolyl, thiadiazolyl, pyrazolyl, tetrazolyl or oxazinyl. The acyl group may be substituted by one to three groups exemplified by a halogen (e.g., chlorine or bromine). Examples of the acyl group include specifically acetyl, propionyl, butyryl, 4-chlorobutyryl, pentanoyl, hexanoyl, benzoyl, naphthoyl, benzylcarbonyl, phenethylcarbonyl, methoxycarbonyl, ethoxycarbonyl, n-propoxycarbonyl, phenoxycarbonyl, benzyloxycarbonyl, thienylcarbonyl, benzothienylcarbonyl and thienyloxycarbonyl. The acyloxy group is a group of the formula A-O- (A is the acyl group as defined above), such as acetoxy, propionyloxy, butyryloxy, pentanoyloxy, hexanoyloxy, benzylcarbonyloxy, phenethylcarbonyloxy, benzoyloxy, naphthoyloxy, thienylcarbonyloxy and benzothienylcarbonyloxy. The acylamino group means an amino group substituted by one or two of the above mentioned acyl groups, such as acetylamino, propionylamino, butyrylamino, 4-chlorobutyrylamino, benzoylamino, benzylcarbonylamino, thienylcarbonylamino, diacetylamino, methoxycarbonylamino, ethoxycarbonylamino, methoxycarbonyl-carbonylamino, ethoxy-carbonyl-carbonylamino, or benzyloxycarbonylamino. The halogen includes fluorine, chlorine, bromine and iodine. The lower alkylamino group means an amino group substituted by one or two of the lower alkyl mentioned above, such as methylamino, ethylamino, n-butylamino, dimethylamino, diethylamino, di-(n-butyl)amino, or cyclohexylamino. The arylamino group means an amino group substituted by one or two of the aryl mentioned above, such as phenylamino or phenylmethylamino. The aralkylamino group means an amino group substituted by one or two of the aralkyl mentioned above, such as benzylamino, 1-phenylethylamino, 2-phenylethylamino, benzhydrylamino or tritylamino. Examples of the organic residue of $R_4$ include the above mentioned lower alkyl, lower alkenyl, lower alkoxy, aryl, aryloxy, aralkyl, aralkyloxy, acyl, acyloxy, acylamino, lower alkylamino, arylamino, aralkylamino and heterocyclic group.

The above mentioned lower alkyl, lower alkenyl, lower alkynyl or lower alkoxy group may be further substituted by one to three of an alkylthio having 1 to 4 carbon atoms (for example, methylthio, ethylthio, n-propylthio or isobutylthio), an arylthio having 6 to 14 carbon atoms (for example, phenylthio), an aralkylthio having 7 to 19 carbon atoms (for example, benzylthio), a halogen (for example, fluorine, chlorine, bromine or iodine), an alkoxy having 1 to 6 carbon atoms (for example, methoxy, ethoxy, n-propoxy, t-butoxy or n-hexyloxy), nitro, carbamoyl, carbamoyloxy, cyano, sulfamoyl, sulfamoyloxy, carboxyl, hydroxyl or/and an acylamino. The acylamino is as defined above.

The aryl, aryloxy, aralkyl or aralkyloxy group as mentioned above may be further substituted on its aromatic ring substituted by one to three of a lower alkyl, a lower alkenyl, a lower alkynyl, a lower alkoxy, an acyl, an acyloxy, nitro, cyano, a halogen, an acylamino or/and an alkylthio having 1 to 4 carbon atoms (for example, methylthio, ethylthio, n-propylthio or t-butylthio). The lower alkyl, lower alkenyl, lower alkynyl, lower alkoxy, acyl, acyloxy, halogen and acylamino as mentioned before are here applicable.

The carbamoyl, thiocarbamoyl, carbamoyloxy, sulfamoyl or sulfamoyloxy group as mentioned above may be further substituted by one or two of a lower alkyl, lower alkoxy, aryl or/and aralkyl. The lower alkyl, lower alkoxy, aryl and aralkyl as mentioned before are here applicable. The lower alkyl group and the lower alkoxy group defined by $R_1$ are applicable to the lower alkyl group and lower alkoxy group of $R_2$ or $R_3$.

Preferably, $R_1$ is a phenyl group which may be substituted by one to three of an acylamino, a lower alkoxycarbonyl, a lower alkyl group which may be substituted by one to three of a halogen, a sulfamoyl group which may be substituted by one or two of a lower alkyl, a lower alkoxy group which may be substituted by one to three of a halogen, cyano, a halogen, nitro or/and a lower alkylsulfonyl.

More preferably, $R_1$ is a group of the formula

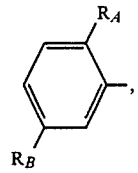

wherein $R_A$ is an acylamino group; a lower alkoxycarbonyl group; a lower alkyl group which may be substituted by one to three of a halogen; a sulfamoyl group which may be substituted by one or two of a lower alkyl; a lower alkoxy group which may be substituted by one to three of a halogen; cyano; a halogen; nitro or a lower alkylsulfonyl group; and $R_B$ is hydrogen, a lower alkyl or nitro group.

Accordingly, the most preferred compounds among the compound (I) can be represented by the general formula:

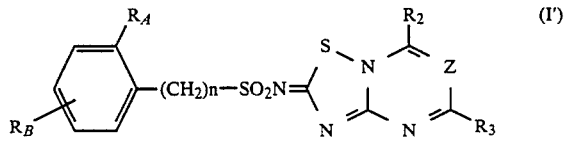
(I')

wherein $R_A$ is an acylamino group; a lower alkoxycarbonyl group, a lower alkyl group which may be substituted by one to three of a halogen; a sulfamoyl group which may be substituted by one or two of a lower alkyl; a lower alkoxy group which may be substituted by one to three of a halogen; cyano; halogen; nitro or a lower alkylsulfonyl group; $R_B$ is hydrogen, a lower alkyl group or nitro, $R_2$ and $R_3$ are a lower alkyl or lower alkoxy group; Z is CH or N and n is 0 or 1.

Here, those defined in $R_1$ are applicable to the acylamino, lower alkoxycarbonyl, lower alkyl which may be substituted by one to three of a halogen, sulfamoyl which may be substituted by one or two of a lower alkyl, lower alkoxy which may be substituted by one to three of a halogen, and lower alkylsulfonyl group of the symbol $R_A$ and the lower alkyl group of the symbol $R_B$.

Examples of the compounds (I) possessing an excellent herbicidal activity are: (1) in case of n being 0, $R_A$ is the halogen; lower alkoxycarbonyl; lower alkyl; lower alkyl which may be substituted by one to three of a halogen; lower alkoxycarbonylamino; lower alkylcarbonylamino which may be substituted by one to three of a halogen; or lower alkoxycarbonylcarbonylamino; and $R_B$ is hydrogen or the lower alkyl. The lower alkyl group of $R_B$ is preferred to be substituted at the 6 position of the phenyl group. Examples of the compounds possessing a further excellent activity are those of $R_A$ being the halogen, lower alkoxycarbonyl or lower alkyl, more preferably the lower alkoxycarbonyl or lower alkyl; and $R_B$ being hydrogen.

(2) in case of n being 1, $R_A$ is the halogen; lower alkoxycarbonyl; lower alkyl which may be substituted by one to three of a halogen; lower alkoxy which may be substituted by one to three of a halogen; lower alkylsulfonyl; sulfamoyl which may be substituted by one or two of a lower alkyl; cyano; or nitro; and $R_B$ is hydrogen or nitro. The nitro group of $R_B$ is preferred to be substituted at the 6 position of the phenyl group. Most preferred examples are those of $R_A$ being the lower alkoxycarbonyl and $R_B$ being hydrogen.

Preferred ones of $R_2$ and $R_3$ respectively are a lower alkyl group having 1 to 4 carbon atoms (for example, methyl, ethyl, n-propyl, isopropyl, n-butyl or tert-butyl) or a lower alkoxy group having 1 to 4 carbon atoms (for example, methoxy, ethoxy, n-propoxy, isopropoxy, n-butoxy or tert-butoxy). The most preferred ones of $R_2$ and $R_3$ respectively are methyl or methoxy.

In case of having a basic group such as amino as the substituent, the compounds (I) may form conventional acid addition salts thereof, e.g. the salts with an organic acid such as trifluoroacetic acid, methanesulfonic acid, p-toluenesulfonic acid or formic acid; or an inorganic acid such as hydrochloric acid, sulfuric acid or phosphoric acid.

In case where an acidic group such as mercapto, hydroxy, sulfo or carboxyl exists in the molecule, the compounds (I) may form conventional base salts thereof, e.g. the salts with an inorganic base such as alkali metal (for example, sodium or potassium) or alkaline earth metal (for example, calcium), or an organic base such as organic tertiary amine, e.g. trimethylamine, triethylamine, tert-butyldimethylamine, dibenzylmethylamine, benzyldimethylamine N,N-dimethylaniline, pyridine or quinoline.

It should be understood that the compounds (I) stated in the specification also include acid addition salts and base salts thereof.

The compounds (I) exhibit in an extremely low application amount an excellent herbicidal effect against a broad range of weeds, for example, paddy weeds such as *Echinochloa oryzicola, Cyperus difformis, Scirpus juncoides, Monochoria vaginalis, Sagittaria pygmaea, Eleocharis acicularis, Cyperus serotinus, Eleocharis kuroguwai, Alisma canaliculatum, Sagittaria trifolia, Scirpus wallichii, Lindernia procumbens, Rotala indica, Potamogeton distinctus, Ludwiga prostrata* or *Flatine triandra*, and field weeds, such as *Digitaria adscendens, Setaria viridis, Amaranthus viridis, Abutilon theophrasti, Chenopodium album, Polygonum longisetum, Portulaca oleracea, Sida spinosa, Datura stramonium, Ipomoea purpurea, Xanthium strumamium, Echinochloa crus-galli, Panicum dichotaomiflorum, Sorghum halepense, Cyperus rotundus, Avena fatua, Alopecurus mvosuroides, Bromus tectorum, Stellaria media, Brassica Sp., Cassia obtusifolia, Matricaria chamomilla* or *Commelina communis*. Moreover, they exhibit no substantial damage on crops such as rice, wheat, barley, corn, soybean, etc. and show a high grade of safety.

The compounds (I) of where n is 1 are highly suitable as herbicides for paddy field, because they exhibit more excellent herbicidal effects on paddy weeds than the compounds (I) where n is 0 and show less damage on rice. Also, the compounds (I) wherein n is 0 are highly useful as herbicides for field, because they exhibit more excellent herbicidal effects on field weeds than the compounds (I) where n is 1 and show less damage on crops such as soybean or corn.

Anyway, the compounds (I) exhibit an excellent herbicidal effect selectively on various weeds only, and not on cops, and are only slightly toxic to , fishes and shellfishes. Therefore, they can be used as herbicides for paddy field, field (farm field), orchard or non-farming land, in extremely high safety, without polluting the environment.

The compounds (I) can be used as herbicide in any application form suited for general agricultural chemicals. That is, one, two, or more than two kinds of the compounds (I) are used in the form of preparation such as emulsifiable concentrates, oil solution, sprays, wettable powders, dusts, DL(Driftless)-type dusts, granules, fine granules, fine granules F, tablets or the like, according to the purpose of use, by dissolving or dispersing them in suitable liquid carriers or mixing them with or adsorbing them on suitable solid carriers. These preparations may contain, if necessary, emulsifying agent, suspending agent, spreading agent, penetrating agent, wetting agent, thickening agent, stabilizer, etc., and can be prepared by any conventional method known per se., e.g. mixing each ingredient.

Suitable examples of the liquid carriers (solvents), include solvents such as water, alcohols (for example, methanol, ethanol, n-propanol, isopropanol or ethylene gylcol), ketones (for example, acetone or methyl ethyl ketone), ethers (for example, dioxane, tetrahydrofuran, ethylene glycol monomethyl ether, diethylene glycol monomethyl ether or propylene glycol monomethyl ether), aliphatic hydrocarbons (for example, kerosine, kerosene oil, fuel oil or machine oil), aromatic hydrocarbons (for example, benzene, toluene, xylene, solvent naphtha or methylnaphthalene), halogenated hydrocarbons (for example, dichloromethane, chloroform or carbon tetrachloride), acid amides (for example, dimethyl formamide or dimethyl acetamide), esters (for example, ethyl acetate, butyl acetate or fatty acid glycerol ester), nitriles (for example, acetonitrile or propionitrile). These solvents are used individually or as a suitable mixture of two, or more, of them.

Suitable examples of the solid carriers (diluents or dust carriers) include vegetable powder (for example, soybean meal, tobacco meal, wheat flour or wood flour), mineral powder (for example, clays such as kaolin, bentonite, or acid clay, talcs such as talc powder or pyrophyllite powder), silicas (for example, diatomaceous earth or mica powder, etc.), aluminas, sulfur powder or active carbon are suitably used. They are used individually or as a suitable mixture of two, more, of them.

As surface active agents used as the emulsifying agent, spreading agent, penetrating agent or suspending agent, if necessary use can be made if necessary use can be made of nonionic or anionic surface active agents such as soaps alkylaryl ethers (e.g. Noigen EA 142 ® from Dai-ichi Kogyo Seiyaku K.K., Japan): polyoxyethylene aryl esters (e.g. Nornal ® from Toho Chemical K.K., Japan); alkylsulfates (e.g. Emal 10 ® and Emal 40 ® from Kao Soap K.K., Japan); alkyl sulfonates (e.g. Neogen ® and Neogen T ® from Dai-ichi Kogyo Seiyaku CO. and Neopelex ® Kao Soap K.K.); polyethylene glycol ethers (e.g. Nonipol 85 ®, Nonipol 100 ® Nonipol 160 ® from Sanyo Kasei K.K., Japan); or polyhydric alcohol esters (e.g. Tween20 ® and Tween 80 ® from Kao Soap K.K.).

The amount of the compound (I) contained in the herbicidal composition is suitably about 1 to 90% by weight in the case of emulsifiable concentrate or wettable powders, about 0.01 to 10% by weight in the case of oil solution, dusts or DL-type dusts and about 0.05 to 10% by weight in the case of fine granules F or granules. However, such concentration may be changed properly, depending on the purpose of use. Emulsifiable concentrates, wettable powders or the like are suitably diluted or extended (for example, to 100 to 100000 times) with water or the like, on the occasion of use, and then scattered.

When the compound (I) is used as a herbicide, its amount may vary depending on the place, the season and the method of application, the kinds of target weeds, the kinds of culture crops, and so on. However, an active ingredient (the compound (I) or its salt) is used in general, in an amount of about 0.05 to 50 g, preferably about 0.1 to 5 g, per 1 are of paddy field and in an amount of about 0.05 to 20 g, preferably about 0.1 to 5 g, per 1 are of field.

For paddy field weeds, it is suitable to use the compound (I) in the soil treatment before germination or in the stem and leaf treatment after germination.

For example, the herbicidal preparation of this invention can be used in safety just after the rice-planting or even 2 to 3 weeks after the planting without revealing any harmful effect, and its effect on the rice continues for a long period of time.

The herbicidal composition of this invention can be used, as occasion demands, in combination with or as an admixture with other herbicidal agent, plant-growth regulating agent, fungicidal agent (for example, organochlorine series fungicide, organosulfur series fungicide or azole series fungicide, antibiotics), insecticidal agent (for example, pyrethroid series insecticides, organophosphorus series insecticide or carbamate series insecticide), and also with miticide, nematocide, synergist, attractant, repellent, dyestuff, fertilizer and the like.

The compound (I) can be prepared according to the process known per se [for example, the process described in Journal of Heterocyclic Chemistry 20, 1127(1983)]. Further, the compound (I) can be prepared, for example, by cyclizing a compound of the general formula (II) [hereinafter abbreviated as the compound (II)].

The compound (II) may be used as salt thereof, to which salt of the compound (I) is similarly applicable. The compound (II) stated in the specification should be understood to include salt thereof.

The cyclization of the compound is achieved by conducting an oxidative dehydrogenation reaction.

The reaction is conducted by contacting the compound (II) with an oxidizing agent. Suitable examples of the oxidizing agents include halogenating agents such as halogen (for example, chlorine, bromine or iodine), N-halogenosuccinimides (for example, N-chlorosuccinimide or N-bromosuccinimide), N-halogenoacetamides (for example, N-chloroacetamide or N-bromoacetamide), N-halogenophthalimide (for example, N-chlorophthalimide or N-bromophthalimide), chloramine T or hypohalogenites (for example, sodium hypochlorite, potassium hypochlorite, calcium hypochlorite or sodium hypobromite); sulfonylhalides such as arylsulfonyl halides (for example, benzenesulfonyl chloride or p-toluenesulfonyl chloride), alkylsulfonyl halides (for example, methanesulfonyl chloride or ethanesulfonyl chloride) or sulfuryl chloride; hydrogen peroxide; peroxy acid such as performic acid, peracetic acid, perpropionic acid, perbenzoic acid, monoperphthalic acid, trifluoroperacetic acid; persulfates, such as sodium persulfate, potassium persulfate or ammonium persulfate; metal-containing oxidizing agents such as seleninum dioxide, manganese dioxide, silver oxide, lead oxide, mercury oxide, ferric chloride, lead tetraacetate, potassium ferricyanide, permanganates or dichromates. Further, nitric acid, oxygen or air is also usable.

The amount of the oxidizing agent employed in the cyclization may suitably be an amount necessary for completing the reaction but theoretically an amount for generating about 0.5 mole of active oxygen, per 1 mole of the compound (II) as the raw material. When the oxidizing agent employed does not generate oxygen, it may be used in an amount to be able to remove about 1 mole of hydrogen, per 1 mole of the compound (II). It is generally not desirable to use too much excess amount of the oxidizing agent because it causes side reactions.

The reaction is generally conducted in a solvent which does not hamper the reaction. Examples of suitable solvent include inert solvents, such as water, alcohols (for example, methanol, ethanol, n-propanol, isopropanol, n-butanol or tertbutanol), aromatic hydrocarbons (for example, benzene, toluene, xylene, nitrobenzene or chlorobenzene) or a halogenated hydrocarbon (for example, dichloromethane, chloroform or carbon tetrachloride), ethers [for example, ethyl ether, dioxane, isopropyl ether, tetrahydrofuran (hereinafter, abbreviated as THF)], ketones (for example, acetone, or methyl ethyl ketone), nitriles (for example, acetonitrile or propionitrile), amides [for example, dimethylformamide (abbreviated as DMF), dimethylacetamide (abbreviated as DMAC), hexamethylphosphoramide (abbreviated as HMPA)], esters (for example, methyl acetate, ethyl acetate or butyl acetate), sulfoxides (for example, dimethylsulfoxide (abbreviated as DMSO), aliphatic carboxylic acids (for example, formic acid, acetic acid or propionic acid), or tertiary organic amines (for example, pyridine, γ-collidine, quinoline, triethylamine, tri-n-propylamine or N,N-dimethylaniline). These solvents may be used individually, or a mixture of two or more kinds thereof with optional ratios.

The cyclization may be conducted in the presence of a base in order to proceed smoothly. Examples of suitable base include inorganic bases such as alkali metal hydroxides (for example, potassium hydroxide or sodium hydroxide), alkaline earth metal hydroxides (for example, calcium hydroxide), alkali metal carbonates (for example, potassium carbonate or sodium carbonate), alkali metal hydrogen carbonate (for example, potassium hydrogen carbonate or sodium hydrogen carbonate), alkaline earth metal carbonates (for example, calcium carbonate) or ammonia; or organic bases such as organic tertiary amines for example, pyridine, collidine, quinoline, triethylamine, tri-n-propylamine, N,N-dimethylbenzylamine, N,N-dimethylaniline, 1,8-diazabicyclo[5.4.0]-7-undecene (abbreviated as DBU), 1,4-diazabicyclo[2.2.2]octane (abbreviated as DBO) or 1,5-diazabicyclo[4.3.0]non-5-ene (abbreviated as DBN). The base may be used in about 0.5 to 3 moles, per 1 mole of the compound (II).

Any of the oxidizing agents mentioned above may be used. However, more excellent oxidizing agents are halogenating agents such as chlorine, bromine, iodine, N-chlorosuccinimide, N-bromosuccinimide, N-bromoacetamide, N-bromophthalimide or chloroamine T; or sulfonylchlorides such as sulfuryl chloride, benzenesulfonyl chloride, p-toluenesulfonyl chloride or methanesulfonyl chloride.

When the reaction is conducted in the presence of a base, it proceeds more smoothly because solubility of the starting compound (II) in solvent is increased, and affords less by-products.

The compound (II) may be isomerized in the presence of a base into the form of the compound shown the general formula:

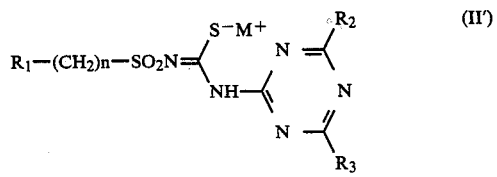

(II')

wherein M+ is an alkali metal ion, 1/2++ (X being an alkaline earth metal) or ammonium ion, and the other symbols have the same meanings as defined above.

In the above mentioned formula, the alkali metal in the alkali metal ion of M+ includes for example lithium, sodium or potassium; the alkaline earth metal in X+ (X being alkaline earth metal) includes magnesium, calcium and barium; and the ammonium ion includes for example ammonium ion which is formed by combining the above mentioned organic tertiary amine with proton. The compound (II) may be isolated from the solution containing the same in accordance with a method known per se and used as the raw material of this cyclization instead of the compound (II).

The reaction temperature is in the range of about $-60°$ C. $\sim 100°$ C. from which a temperature is selected which will cause the reaction to proceed but generally a suitable temperature is between about $-20°$ C. and $50°$ C. The reaction time is comparatively short, e.g., about 5 minutes to 2 hours but in most cases the reaction is almost complete when all of the oxidizing agent is added.

The completion of the reaction can be easily confirmed by means of thin layer chromatography or high-performance liquid chromatography. The compound (I) thus obtained can be isolated and purified by a known isolation and purification means per se such as concentration, concentration under reduced pressure, change of acidity or alkalinity, phase transfer, solvent extraction, crystallization, recrystallization or chromatography.

The compounds (II) can be used as the starting materials for the compounds (I) of the present invention. In addition, the compounds (II) themselves are useful as selective herbicidal agents and may be used in the same way as the compounds (I).

The compounds (II) can be prepared by any of Production Methods 1 to 3.

Production Method 1

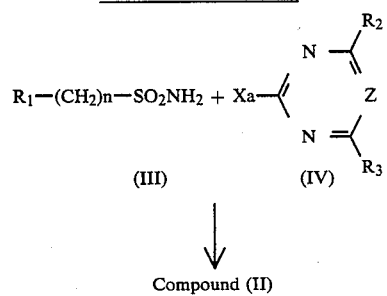

In the above formulae, $X_a$ is isocyanato or monoor bis-(phenoxythiocarbonyl)amino and the other symbols have the same meanings as defined above.

In the reaction, the compound (IV) is used in about 0.8 to 8 moles, preferably about 0.9 to 1.3 moles, per 1 mole of the compound (III).

The reaction is generally conducted in an inert solvent. Examples of suitable solvent include aromatic hydrocarbons such as benzene, toluene or xylene, halogenated hydrocarbons such as dichloromethane, chloroform or carbon tetrachloride, ethers such as ethyl ether, isopropyl ether, dioxane or THF, nitriles such as acetonitrile or propionitrile, esters such as ethyl acetate, hydrocarbons such as petroleum ether, petroleum benzine or hexane, and ketones such as acetone or methyl ethyl ketone, which may be used individually or as a mixture thereof.

The reaction may be conducted in the presence of a base.

Examples of suitable base include organic bases such as tri(alkyl having 1 to 6 carbon atoms)-substituted amines (for example, trimethylamine or triethylamine) or tertiary amines (for example, pyridine, γ-collidine, DBU, DBO or DBN; or inorganic bases such as alkali metal hydroxides (for example, potassium hydroxide or sodium hydroxide), alkaline earth metal hydroxides (for example, calcium hydroxide), alkali metal carbonates (for example, potassium carbonate or sodium carbonate), alkali metal hydrogen carbonates (for example, potassium hydrogen carbonate or sodium hydrogen carbonate) or alkaline earth metal carbonates (for example, calcium carbonate).

The base may be used in about 0.8 to 1.2 moles, per 1 mole of the compound (IV).

The reaction temperature may be selected from the range of 0 to 150° C. but generally about 10° to 60° C. is suitable The reaction is completed in 30 minutes to 10 hours, and its completion can be confirmed by means of thin layer chromatography or high-performance liquid chromatography.

The compound (III), (VIII) or (IX) may be in the form of acid addition salt or base salt thereof, to which the salts of the compound (I) are similarly applicable. The compound (III), (VIII) or (IX) stated in the specification includes salt thereof.

Production Method 2

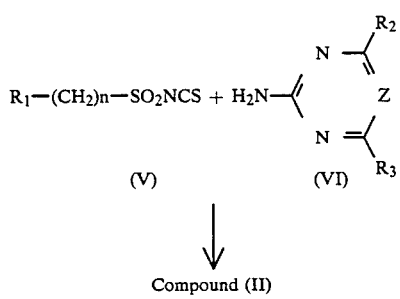

Compound (II)

The symbols in the above formulae have the same meanings as defined above.

The compound (VI) may be in the form of acid addition salt thereof with an organic acid such as trifluoroacetic acid, methanesulfonic acid, p-toluenesulfonic acid or formic acid, or an inorganic acid such as hydrochloric acid, sulfuric acid or phosphoric acid, In the reaction, the compound (V) is used in about 0.8 to 3.0 moles, preferably abut 0.9 to 1.3 moles, per 1 mole of the compound (VI) or salt thereof.

The reaction is generally conducted in an inert solvent. Examples of suitable solvents include aromatic hydrocarbons such as benzene, toluene or xylene, halogenated hydrocarbons such as dichloromethane, chloroform or carbon tetrachloride, ethers such as ethyl ether, isopropyl ether, dioxane or THF, nitriles such as acetonitrile or propionitrile, esters such as ethyl acetate, hydrocarbons such as petroleum ether, petroleum benzine or hexane, and ketones such as acetone or methyl ethyl ketone, which may be used individually or as a mixture thereof.

The reaction may be conducted in the presence of a base.

Examples of suitable bases include organic bases such as DBU, DBO, DBM, triethylamine, tri-n-propylamine or pyridine; and inorganic bases such as sodium amide or sodium hydride.

The base may be used in about 0.8 to 2.5 moles, per 1 mole of the compound (VI).

The reaction temperature may be selected from the range of about 0° to 150° C. but is generally about 10° to 100° C. The reaction is completed in 30 minutes to 10 hours, and its completion can be confirmed by means of thin layer chromatography or high performance liquid chromatography.

Production Method 3

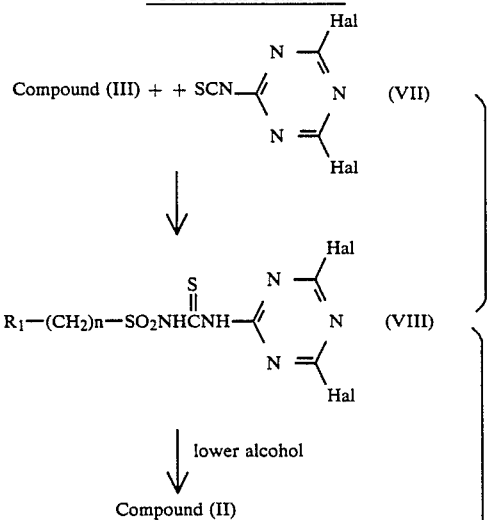

Compound (II)

(provided that in the formula (II), $R_1$ and n have the same meanings as defined above, Z is N, and $R_2$ and $R_3$ respectively are lower alkoxy).

In the above formulae, $R_1$ and n have the same meanings as defined above, and Hal is a halogen such as chlorine or bromine. The lower alkoxy group defined in $R_1$ is applicable to that in $R_2$ and $R_3$.

The 1st step of the reaction is to react the compound (III) with the compound (VII) to prepare the compound (VIII).

The compound (VII) of the starting material is used in about 0.8 to 2.0 moles, per 1 mole of the compound (III).

The reaction is generally conducted in an inert solvent. Examples of suitable solvent include aromatic hydrocarbons such as benzene, toluene or xylene, halogenated hydrocarbons such as dichloromethane, chloroform or carbon tetrachloride, ethers such as ethyl ether, isopropyl ether, dioxane or THF, nitriles such as acetonitrile or propionitrile, esters such as ethyl acetate, and hydrocarbons such as petroleum ether, petroleum benzine or hexane, which may be in individually or mixture thereof.

The reaction may be conducted in the presence of a base. Examples of suitable base include organic bases such as tri(alkyl having 1 to 6 carbon atoms)-substituted amines (for example, trimethylamine or triethylamine) or tertiary amines (for example, pyridine, γ-collidine, DBU, DBO or DBN; and inorganic bases such as alkali metal hydroxides (for example, potassium hydroxide or sodium hydroxide), alkaline earth metal hydroxides (for example, calcium hydroxide), alkali metal carbonates (for example, potassium carbonate or sodium carbonate), alkali metal hydrogen carbonates (for example, potassium hydrogen carbonate or sodium hydrogen carbonate) or alkaline earth metal carbonates (for example, calcium carbonate).

The base may be used in about 0.8 to 1.2 moles, per 1 mole of the compound (VII).

The reaction temperature may be selected from the range of about 0° to 100° C. The reaction time is about 30 minutes to 10 hours.

The compound (VIII) thus obtained may be subjected to the next reaction as it is in the reaction solution or after it is isolated and purified by a known means per se.

The 2nd step of the reaction is to react the compound (VIII) with a lower alcohol to prepare the compound (II) ($R_1$ having the same meaning as defined above and $R_2$ and $R_3$ respectively being a lower alkoxy).

Examples of the lower alcohol employed in the reaction are alcohols having 1 to 6 carbon atoms such as methanol, ethanol, n-propanol, tert-butanol or n-hexanol.

The lower alcohol is used in about 2 to 10 moles, per 1 mole of the compound (VIII) but may be used in a large excess amount, serving as solvent.

The reaction may be conducted in an inert solvent. Examples of suitable solvent include aromatic hydrocarbons such as benzene, toluene or xylene, halogenated hydrocarbons such as dichloromethane, chloroform or carbon tetrachloride, ethers such as ethyl ether, dioxane or THF, ketones such as acetone or methylethylketone, nitriles such as acetonitrile or propionitrile, amides such as DMF, DMAC or HMPA, esters such as methyl acetate or ethyl acetate, and sulfoxides such as DMSO, which may be used individually or as mixture thereof.

The reaction temperature is about room temperature to 120° C., and the reaction time is about 30 minutes to 10 hours.

The compound (II) thus obtained can be isolated and purified by an isolation and purification means known per se, such as concentration, concentration under reduced pressure, change of acidity or alkanility, phase transfer, solvent extraction, crystallization, recrystallization or chromatography.

The compound (III) which is the raw material of Production Methods 1 and 3 for the compound (II) can be easily prepared by a method known per se or analogus method thereto. The compound (III) can be prepared for example by the method shown by the following reaction scheme.

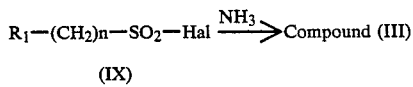

$$R_1-(CH_2)n-SO_2-Hal \xrightarrow{NH_3} \text{Compound (III)}$$

(IX)

The symbols in the formulae have the same meanings as defined above.

The compound III) is prepared by reacting the compound (IX) with ammonia.

Ammonia is used in an amount of about 1 to 100 moles, preferably about 2 to 30 moles, per mole of the compound (IX).

The reaction is usually conducted in a solvent. Examples of suitable solvent include water, alcohols such as methanol, propanol or butanol, dimethylsulfoxide, DMF, DMAC, glymes such as methylcellosolve, dimethylcellosolve or diethyleneglycol dimethylether, polar solvents such as dioxane, THF or acetonitrile, or mixture thereof, and a mixture of the polar solvent and a nonpolar solvent such as chloroform or dichloromethane. The reaction temperature is not particularly limited but usually is in the range of −40~50° C. The reaction temperature is usually about several minutes to 24 hours.

The compound (IX) can be prepared by methods known per se, for example, those described in Journal of Chemical Society 1958, p2903; Journal of Organic Chemistry 25, 1824(1960); Organic Functional Group Preparations 1, 516(1972) (Academic Press, New York & London); Journal of the American Chemical Society 58, 1348(1936); and Journal of Organic Chemistry 16, 621(1951) or analogus methods thereto.

The compound of the general formula (IV) can be easily prepared by various methods, for example those described in Japanese Unexamined Pat. Publication No. 143686/1976; Tetrahedron 29, 691(1973) and Japanese Pat. Application No. 244892/1986 or analogus methods thereto.

The sulfonylisothiocyanates of the general formula (V) can be easily prepared by methods described in Angewandte Chemie, International Edition 4, 430(1965); Archiv der Pharmazie 299, 174(1966); Chemical Abstracts 64, 15783e(1966) and Chemische Berichte 99, 2885(1966) and analogus methods thereto. The compounds of the general formula (VI) can be prepared by methods known per se.

The following symbols used in Reference Examples and Examples mean as follows.
s: singlet, d: doublet, t: triplet
q: quartet, m: multiplet, Me: methyl
Et: ethyl In the chromatography, numerical values parenthesized for mixture solvents as an eluent mean the ratios by volume of each solvent mixed.

The percentage (%) means % by weight, unless otherwise specified.

REFERENCE EXAMPLE 1

2-Isothiocyanato-4-methoxy-6-methylpyrimidine

A mixture of 4.2 g of 4-methoxy-6-methyl-2-trimethylsilylaminopyrimidine and 3.5 g of phenyl chlorothionocarbonate in 30 ml of toluene is stirred with heating at ca. 80° C. for 5.5 hours. The reaction solution is cooled to room temperature and filtered to remove the precipitate. The filtrate is concentrated under reduced pressure, and the residue is purified by silica gel chromatography (eluent: ethyl acetate: toluene =1:3) to give the title compound (2.3 g). mp 54°~55° C.

IR $\nu$(nujol)cm$^{-1}$: 1990, 1595, 1560, 1350, 1200, 1045.

REFERENCE EXAMPLE 2

Phenyl N-(4,6-dimethoxypyrimidin-2-yl)thionooarbamate

Phenyl chlorothionocarbonate (0.82 g) is dropwise added to a solution of 1.0 g of 2-amino-4,6-dimethoxypyrimidine in 10 ml of THF with stirring at room temperature and during 5 minutes, and then refluxed for 7 hours. The reaction mixture is cooled to room temperature, and filtered to remove the precipitate. The filtrate is concentrated under reduced pressure. The residue is purified by silica gel column-chromatography (eluent: chloroform) to give 0.1 g of the title compound. mp 114° C.

IR $\nu$(nujol)cm$^{-1}$: 3200, 1605, 1530, 1325, 1195.

REFERENCE EXAMPLE 3

4,6-Dimethoxy-2-isothiocyanatopyrimidine

A solution of 45.0 g of 4,6-dimethoxy-2-trimethylsilylaminopyrimidine and 35.0 g of phenyl chlorothionocarbonate in 300 ml of acetonitrile is refluxed for 10 hours. The reaction solution is concentrated under reduced pressure to remove acetonitrile. Toluene (300 ml) is added to the residue and filtered to remove insoluble substance. The filtrate is concentrated under reduced pressure and purified by silica gel column-chromatography (eluent: ethyl acetate:hexane =1:1). 4,6-Dimethoxy-2-isothiocyanatopyrimidine (17.0 g) is obtained from the first eluate. mp 85°~86° C.

IR ν(liquid film)cm⁻¹: 1995.

2-[N,N-Bis(phenoxythiocarbonyl)amino]-4,6-dimethoxypyrimidine (3.5 g) is obtained from the later eluate. mp 127~128° C.

IR ν(nujol)cm⁻¹: 1600, 1295, 1190.

REFERENCE EXAMPLE 4

4,6-Dimethyl-2-isothiocyanatopyrimidine

The title compound as pale yellowish oil is obtained by using 4,6-dimethyl-2-trimethylsilylaminopyrimidine and phenyl chlorothionocarbonate and treating in a similar way to Reference Example 3.

bp 117°~118° C./2 mmHg
IR ν(liquid film)cm⁻¹: 1995.

REFERENCE EXAMPLE 5

4-Methoxy-6-methyl-2-isothiocyanato-1,3,5-triazine

A solution of 15.0 g of 4-methoxy-6-methyl-2-trimethylsilylamino-1,3,5-triazine and 12.2 g of phenyl chlorothionocarbonate in 50 ml of xylene is stirred for 6.5 hours at ca. 140° C. The reaction solution is cooled to room temperature, and filtered to remove insoluble substance, and the resulting filtrate is concentrated under reduced pressure. The residue is purified by silica gel column-chromatography (eluent: ethyl acetate:toluene =1:3) to give 3.0 g of the title compound as an oil.

IR ν(liquid film)cm⁻¹: 1970.

REFERENCE EXAMPLE 6

4,6-Dimethyl-2-isothiocyanato-1,3,5-triazine

The title compound is obtained as a pale yellow oil by using 4,6-dimethyl-2-trimethylsilylamino-1,3,5-triazine and phenyl chlorothionocarbonate and treating in a similar way to Reference Example 5.

IR ν(liquid film)cm⁻¹: 1960.

REFERENCE EXAMPLE 7

2-Ethoxycarbonylbenzenesulfonamide

A solution of 3.5 g of ethyl chloroformate in 10 ml of anhydrous acetonitrile is dropwise added to a solution of 5.5 g of 2-aminobenzenesulfonamide and 2.5 g of pyridine in 80 ml of anhydrous acetonitrile at room temperature during 2 hours. After stirring at room temperature, the mixture is poured into ice water and acidified with 100 ml of 2N-hydrochloric acid solution. The mixture is extracted with ethyl acetate twice, washed with an aqueous saturated sodium hydrogen carbonate and then with a saturated brine, and dried over anhydrous sodium sulfate. Then the mixture is concentrated under reduced pressure. The residue is crystallized from chloroform to give 6.6 g of the title compound.

NMR(d-DMSO)δ ppm: 1.27(3H,t), 4.20(2H,q), 7.17-8.23 (8H,m), 8.97(1H,s).

REFERENCE EXAMPLE 8

2,6-Dimethylbenzenesulfonamide

Conc. hydrochloric acid (20 ml) is added to 50 ml of water, to which 12.1 g of 2,6-dimethylaniline is dissolved. To this solution, a solution of 6.9 g of sodium nitrite in 25 ml of water is added at −5°~0° C. to make a diazonium salt solution.

On the other hand, 26.4 g of sodium sulfide 9 hydrate and 3.5 g of sulfur powder are added to 30 ml of water to make a sodium disulfide solution. The above diazonium salt solution is portionwise dropped in the sodium disulfide solution, maintaining at −5°~0° C., during which foaming occurs and the disulfide compound is isolated as a red oil. The red oily product separated by extraction using chloroform is dissolved in 50 ml of glacial acetic acid, into which chlorine gas is introduced at 20° C. until no further gas is absorbed. The mixture is poured into ice water to isolate an oily sulfonylchloride compound, which is extracted with methylene chloride. 28 % w/w Ammonia water (10 ml) is dropwise added to the extract under ice-cooling with stirring. The precipitated crystals are collected by filtration and recrystallized from water to give 5.7 g of the title compound. mp 113°~114° C.

IR ν(nujol)cm⁻¹: 3360, 3260, 1455, 1330, 1150.

REFERENCE EXAMPLE 9

2-Ethoxycarbonyl-6-methylbenzenesulfonamide

To 6.0 g of bis(2-hydroxycarbonyl-6-methylphenyl)disulfide obtained in a similar way described in Reference Example 8, is added 20 ml of thionyl chloride, followed by refluxing for 30 minutes. Excess of thionyl chloride is removed off and 20 ml of ethanol is added to the residue to give the ethyl ester compound. This compound is dissolved in 80 ml of glacial acetic acid, into which chlorine gas is introduced at 20° C. until no further gas is absorbed. The reaction mixture is poured into ice water. The precipitated crystals are collected by filtration, washed with water and dried sufficiently.

The crystals are dissolved in 80 ml of dry ether and saturated with ammonia gas at −15° C. The title compound (4.5 g) as a prism is obtained from the ether layer.
mp 93°~94° C.

IR ν(nujol)cm⁻¹: 3350, 3240, 1720, 1540, 1460, 1335, 1300, 1160.

REFERENCE EXAMPLE 10

S-(2-Methoxycarbonylbenzyl)isothiourea·hydrochloride

A solution of 196 g of methyl 2-chloromethylbenzoate and 83.7 g of thiourea in 500 ml of ethanol is refluxed for 4 hours. The reaction solution is concentrated under reduced pressure and to the resulting residue is added 300 ml of isopropylalcohol. The precipitated crystals are collected by filtration and dried to give 112.8 g of the title compound.

mp 196°~198° C.

NMR(d₆-DMSO)δppm:3.86(3H,s), 4.77(2H,s), 7.30-8.20 (4H,m), 9.34(4H, br.s).

REFERENCE EXAMPLE 11

2-Methoxycarbonylbenzylsulfonamide

S-(2-Methoxycarbonylbenzyl)isothiourea·hydrochloride (125 g) obtained by Reference Example 10 is dissolved in the mixture of 2.4 l of water and 0.8 l of acetic acid, to which chlorine gas is bubbled at −5°~0° C. with stirring until saturation. The precipitated crystals are collected by filtration, washed with cold water and dried to give 88.4 g of (2-methoxycarbonylbenzyl)sulfonyl chloride as crystals of mp 80°~82° C.

Aqueous ammonia (the mixture of 70 ml of aqueous conc. ammonia and 70 ml of water)is dropwise added to a solution of 80.6 g of the above crystals in 300 ml of dichloromethane and stirred for 2.5 hours under cooling. To the reaction solution is added water (150 ml), and the organic layer is separated, washed with cold water, dried over anhydrous sodium sulfate. The organic layer then is distilled to remove dichloromethane, by which 45.7 g of the title compound is obtained. mp 79°~81° C.

NMR(CDCl$_3$)δ ppm:3.92 3H,s , 4.74(2H,s), 4.90(2H,s), 7.20–8.50(4H,m).

The compounds of Table 1 are obtained by a similar way to Reference Examples 10 and 11.

TABLE 1

General formula

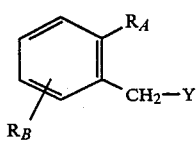

| Compound No. | R$_A$ | R$_B$ | Y | mp (°C.) | |
|---|---|---|---|---|---|
| a | CN | H | S—C(=NH)NH$_2$ | 173–175 | (HCl salt) |
| b | OCHF$_2$ | H | S—C(=NH)NH$_2$ | 166–168 | (HCl salt) |
| c | Me | H | S—C(=NH)NH$_2$ | * | (HCl salt) |
| d | CF$_3$ | H | S—C(=NH)NH$_2$ | * | (HCl salt) |
| e | SO$_2$NMe$_2$ | H | S—C(=NH)NH$_2$ | *a | (HCl salt) |
| f | CN | H | SO$_2$Cl | 83–84 | |
| g | OCHF$_2$ | H | SO$_2$Cl | 29–35 | |
| h | Me | H | SO$_2$Cl | * | |
| i | CF$_3$ | H | SO$_2$Cl | * | |
| j | SO$_2$NMe$_2$ | H | SO$_2$Cl | 110 | |
| k | CN | H | SO$_2$NH$_2$ | 128–130 | |
| l | OCHF$_2$ | H | SO$_2$NH$_2$ | 125–126 | |
| m | Me | H | SO$_2$NH$_2$ | 117 | |
| n | CF$_3$ | H | SO$_2$NH$_2$ | 117–118 | |
| o | SO$_2$NMe$_2$ | H | SO$_2$NH$_2$ | 108–109 | |

*This compound is used in the next reaction without isolation and its structure is confirmed as sulfonamide derivative thereof.

*a This is used in the next reaction without isolation and its structure is confirmed as sulfonylchloride derivative thereof.

REFERENCE EXAMPLE 12

N-(2-Chlorophenylsulfonyl)-N'-(4-methoxy-6-methyl-2pyrimidinyl)thiourea [Compound No.(28)]

A solution of 5.0 g of methyl N-(2-chlorophenylsulfonyl)dithiocarbamate in 20 ml of xylene is stirred for 3.5 hours with heating at 145° C. During the heating, methylmercaptan gas is generated. After the reaction is completed, xylene is removed under reduced pressure to yield a pale yellow oil (IR: strong absorption band of -SO$_2$NCS at 1900 cm$^{-1}$). The oily substance is dissolved in 50 ml of acetonitrile, to which 2.8 g of 2-amino-4-methoxy-6-methylpyrimidine is added and stirred for 30 minutes at 50° C. The precipitated crystals are collected by filtration, and recrystallized from acetonitrile to give 5.6 g of the title compound as a white prism. mp 186.5°~187.5° C.

Elemental analysis for C$_{13}$H$_{13}$ClN$_4$O$_3$S$_2$: Calcd. (%) C:41.87, H:3.51; N:15.03 ; Found (%) C:41.82, H:3.58; N:14.95;

IR ν(nujol)cm$^{-1}$: 3180, 1610, 1525, 1460, 1350

NMR(d$_6$-DMSO)δ ppm:2.53(3H,s), 3.96(3H,s), 6.48(1H,s), 7.40–8.30(4H,m), 11.00(1H,s).

REFERENCE EXAMPLE 13

N-(2-Methoxycarbonylbenzyl)sulfonyl-N'-(4,6-dimethoxy-2-pyrimidinyl) thiourea [Compound No. (16)]

A mixture of 2.5 g of (2-methoxycarbonylbenzyl)sulfonamide, 21.5 g of 4,6-dimethoxy-2-isothiocyanatopyrimidine and 15.1 g of anhydrous potassium carbonate in 400 ml of acetone is stirred for 8.5 hours at 55° C., and then filtered to collect precipitated crystals. To the filtrate, further 2 g of anhydrous potassium carbonate is added and stirred for 2 hours at 60° C. The precipitated crystals are collected. The combined crystals are suspended in 1.5 of water and adjusted to pH 2 with hydrochloric acid. After stirring the mixture for an hour, the crystals are collected by filtration, washed with water, dried and recrystallized from acetonitrile to give 35.9 g of the title compound, as white powder.

mp 167°~168° C.

Elemental analysis for C$_{16}$H$_{18}$N$_4$O$_6$S$_2$: Calcd. (%) C:45.06,H:4.25; N:13.14; Found (%) C:45.02, H:4.18; N:13.42;

IR ν(nujol)cm$^{-1}$3180, 1710, 1610, 1455, 1360.

NMR(d$_6$-DMSO)δ ppm:3.72(6H,s), 3.83(3H,s), 5.31(2H,s), 5.91 (1H,s), 7.40–7.90(4H,m), 10.65(1Hs), 12.07(1H,s).

The compounds of Table 2 are obtained by a similar way to Reference Examples 12 and 13.

TABLE 2

General formula $$R_1-(CH_2)_n-SO_2NH-\overset{S}{\underset{}{C}}-NH-\underset{N}{\overset{N}{\diagdown}}\underset{R_3}{\overset{R_2}{\diagup}}Z$$

| Compd. No. | $R_1$ | n | $R_2$ | $R_3$ | Z | mp (°C.) |
|---|---|---|---|---|---|---|
| (1) | 2-Cl-phenyl | 0 | Me | MeO | N | 160–161 |
| (2) | 2-COOMe-phenyl | 0 | Me | Me | CH | 171–173 |
| (3) | 2-COOMe-phenyl | 0 | Me | MeO | CH | 161–163 |
| (4) | 2-COOMe-phenyl | 0 | MeO | MeO | CH | 178–179 |
| (5) | 2-COOMe-phenyl | 0 | Me | MeO | N | 144–145 |
| (6) | 2,3-diMe-phenyl | 0 | MeO | MeO | CH | (½MeCN cont.) 167–168 (decomp.) |
| (7) | 2-NHCOCOOEt-phenyl | 0 | Me | MeO | CH | 130–132 |
| (8) | 2-NHCOCH$_2$CH$_2$CH$_2$Cl-phenyl | 0 | Me | MeO | CH | 122–124 |
| (9) | 2-OCHF$_2$-phenyl | 0 | MeO | MeO | CH | 185–186 |

TABLE 2-continued
General formula
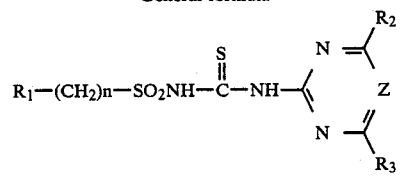
| Compd. No. | $R_1$ | n | $R_2$ | $R_3$ | Z | mp (°C.) |
|---|---|---|---|---|---|---|
| (10) | 2-Cl-C$_6$H$_4$ | 1 | Me | Me | CH | 170–171 |
| (11) | 2-Cl-C$_6$H$_4$ | 1 | Me | MeO | CH | 166–167 |
| (12) | 2-Cl-C$_6$H$_4$ | 1 | MeO | MeO | CH | 185–186 |
| (13) | 2-Cl-C$_6$H$_4$ | 1 | Me | MeO | N | 169–170 |
| (14) | 2-COOMe-C$_6$H$_4$ | 1 | Me | Me | CH | 155–157 |
| (15) | 2-COOMe-C$_6$H$_4$ | 1 | Me | MeO | CH | 157–159 |
| (17) | 2-COOMe-C$_6$H$_4$ | 1 | Me | MeO | N | 144–145 |
| (18) | 2-COOMe-C$_6$H$_4$ | 1 | MeO | MeO | N | 159–160 |
| (19) | 2-COOMe-3-NO$_2$-C$_6$H$_3$ | 1 | MeO | MeO | CH | 188–189 |

TABLE 2-continued

General formula:

$$R_1-(CH_2)_n-SO_2NH-\underset{\underset{S}{\|}}{C}-NH-\underset{N=}{\overset{N=}{\underset{}{}}}\underset{R_3}{\overset{R_2}{\underset{}{\diagdown}}}Z$$

| Compd. No. | $R_1$ | n | $R_2$ | $R_3$ | Z | mp (°C.) |
|---|---|---|---|---|---|---|
| (20) | 2-CN-phenyl | 1 | Me | Me | CH | 152 (decomp.) |
| (21) | 2-CN-phenyl | 1 | Me | MeO | CH | 174 (decomp.) |
| (22) | 2-CN-phenyl | 1 | MeO | MeO | N | 186 (decomp.) |
| (23) | 2-NO$_2$-phenyl | 1 | Me | MeO | CH | 176–177.5 |
| (24) | 2-NO$_2$-phenyl | 1 | MeO | MeO | N | 184–187 |
| (25) | 2-SO$_2$Me-phenyl | 1 | MeO | MeO | CH | 170–172 |
| (26) | 2-CF$_3$-phenyl | 1 | MeO | MeO | CH | 187–189 |
| (27) | 2-OCHF$_2$-phenyl | 1 | MeO | MeO | CH | 187–189 |
| (29) | 2-SO$_2$NMe$_2$-phenyl | 1 | MeO | MeO | CH | 170–172 |

TABLE 2-continued

General formula $$R_1-(CH_2)n-SO_2NH-\overset{\overset{S}{\|}}{C}-NH-\underset{N\overset{}{=\!\!=}}{\overset{N\overset{}{=\!\!=}}{\bigwedge}}\underset{R_3}{\overset{R_2}{Z}}$$

| Compd. No. | $R_1$ | n | $R_2$ | $R_3$ | Z | mp (°C.) |
|---|---|---|---|---|---|---|
| (30) | ![phenyl with COOMe and NO2] COOMe / NO2 | 1 | MeO | MeO | CH | 188–189 |
| (31) | ![phenyl with NO2] NO2 | 1 | MeO | MeO | CH | ** |
| (32) | ![phenyl with NHCOOEt] NHCOOEt | 0 | Me | Me | CH | ** |
| (33) | ![phenyl with COOEt and Me] COOEt / Me | 0 | MeO | MeO | CH | ** |

**This compound is used in the next reaction without isolation and its structure is confirmed as the object compound.

The present invention is further illustrated by the following examples, but is not limited thereto.

EXAMPLE 1

Preparation of 2-(2-chlorophenylsulfonyl)imino-5-methoxy-7-methyl-2H-[1,2,4]-thiadiazolo [2,3-a]pyrimidine (Compound No. 2)

A solution of 2.0 g of N-(2-chlorophenylsulfonyl)-N'-(4-methoxy-6-methyl-2-pyrimidinyl) thiourea in 30 ml of pyridine is cooled to $-6°$ C. $\sim -8°$ C., to which 0.9 g of bromine is dropwise added. After stirring for 1.5 hours, at the same temperature, the reaction mixture is poured into 150 ml of ice water and the precipitate is collected by filtration. It is then washed with water, dried, and recrystallized from acetonitrile to give 1.4 g of title compound as white needles. mp $191° \sim 192°$ C. (decomp.)

Elemental analysis for $C_{13}H_{11}ClN_4O_3S_2$: Calcd. (%) C:42.10, H:2.99; N:15.11; Found (%) C:42.17, H:2.89; N:15.06;

IR $\nu$(nujol)cm$^{-1}$ 1630, 1445, 1375, 1300, 1095, 910.

NMR(d$_6$-DMSO)δ ppm: 2.65(3H,s), 4.04(3H,s), 6.65(1H,s), 7.30–8.30(4H,m).

EXAMPLE 2

Preparation of 5,7-dimethoxy-2-[(2-methoxycarbonylbenzyl)sulfonyl]imino-2H-[1,2,4]-thiadiazolo[2,3-a]pyrimidine (Compound No. 21)

N-(2-Methoxycarbonylbenzyl)sulfonyl-N'-(4,6-dimethoxy-2-pyrimidinyl) thiourea (1.0 g) is dissolved in 15 ml of pyridine and cooled to $-10° \sim -5°$ C., to which 0.4 g of bromine is dropwise added. After stirring for 1.5 hours at the same temperature, the reaction mixture is poured into 100 ml of ice water and the white crystals are collected by filtration. The product is washed with water, dried and washed with hot acetonitrile to give 0.78 g of the title compound as white powdery crystals. mp $153° \sim 154°$ C.

Elemental analysis for $C_{16}H_{16}N_4O_6S_2$: Calcd. (%) C:45.28, H:3.80; N:13.20; Found (%) C:45.24, H:3.72; N:13.42;

IR $\nu$(nujol)cm$^{-1}$ 1715, 1638, 1460, 1360, 1098, 900.

NMR(d$_6$-DMSO)δ ppm: 3.83(3H,s), 4.03(3H,s), 4.15(3H,s), 4.97 (2H,s), 6.45(1H,s), 7.30–7.90(4H,m).

EXAMPLE 3

Preparation of
5,7-dimethoxy-2-[(2-trifluoromethylbenzyl)sulfonyl]imino-2H-[1,2,4]-thiadiazolo[2,3-a]pyrimidine (Compound No. 32)

A suspension of 1.0 g of N-(2-trifluoromethylbenzyl)sulfonyl-N'-(4,6-dimethoxy-2-pyrimidinyl)thiourea in 20 ml of methanol is cooled at −10°∼−5° C., and a solution of 0.12 ml of bromine in 1 ml of methanol is dropwise added to the solution. The temperature of the mixture is gradually raised to room temperature and the mixture is stirred for 2 hours. The crystals are collected by filtration, washed with methanol, dried and recrystallized from acetonitrile to give 0.8 g of the title compound as white crystals.

mp 179°∼181° C.

Elemental analysis for $C_{15}H_{13}N_4O_4S_2F_3$: Calcd.(%) C:41.47, H:3.02; N:12.90; Found (%) C:41.48, H:2.95; N:12.74;

IR $\nu$(nujol)cm$^{-1}$ 1640, 1620, 1550, 1470, 1370, 920.

NMR(d$_6$-DMSO) δ ppm:4.01(3H,s), 4.15(3H,s), 4.61(2H,s), 6.45(1H,s), 7.30-7.90(4H,m).

EXAMPLE 4

Preparation of
5,7-dimethoxy-2-[(2-difluoromethoxybenzyl)sulfonyl]imino-2H-[1,2,4]-thiadiazolo[2,3-a]pyrimidine (Compound No. 33)

To a suspension of 0.5 g of N-(2-difluoromethoxybenzyl) sulfonyl-N'-(4,6-dimethoxy-2-pyrimidinyl)thiourea in 20 ml of methanol is added 0.2 g of N-bromosuccinimide with stirring under ice cooling. After stirring for 30 minutes at the same temperature and further for an hour at room temperature, the crystals are collected by filtration, washed with methanol, and recrystallized from acetonitrile to give 0.3 g of the title compound as white crystals.

mp 151°∼152° C.

Elemental analysis for $C_{15}H_{14}N_4O_5S_2F_2$: Calcd.(%) C:41.66, H:3.26; N:12.92; Found (%) C:41.68, H:3.23; N:12.83;

IR $\nu$(nujol)cm$^{-1}$: 1640, 1540, 1470, 1365, 920.

NMR(d$_6$-DMSO) δ ppm:4.01(3H,s), 4.14(3H,s), 4.47(2H,s), 6.46(1H,s), 7.08(1H,t), 7.00-7.80 (4H,m).

EXAMPLE 5

Preparation of
2-[(2-methoxycarbonyl)phenylsulfonyl]imino-5-methoxy-7-methyl-2H-[1,2,4]-thiadiazolo[2,3-a][1,3,5]-triazine (Compound No. 34)

To a suspension of 2.5 g of N-(2-methoxycarbonyl)phenylsulfonyl-N'-(4-methoxy-6-methyl-1,3,5-triazin-2-yl) thiourea in 50 ml of methanol, 1.2 g of N-bromosuccinimide is portionwise added at −5°∼−10° C. After stirring at the same temperature for further 1.5 hours, the crystals are collected by filtration, washed with methanol, dried and recrystallized from a mixed solvent of acetone and n-hexane to give 2.0 g of the title compound as a white prism.

mp 158°∼159° C. (decomp.).

Elemental analysis for $C_{14}H_{13}N_5O_5S_2$: Calcd.(%) C:42.53, H:3.31; N:17.71; Found (%) C:42.52, H:3.41.; N:17.67;

IR $\nu$(nujol)cm$^{-1}$ 1728, 1622, 1458, 1370, 1100, 903.

NMR (d$_6$-DMSO) δ ppm: 2.71(3H,s), 3.81(3H,s), 4.05(3H,s), 7.61-8.10(4H,m).

Table 3 shows the compounds prepared by a similar way to Examples 1–5.

TABLE 3
General formula

| Compd. No. | $R_A$ | $R_B$ | n | $R_2$ | $R_3$ | Z | mp (°C.) |
|---|---|---|---|---|---|---|---|
| 1 | Cl | H | 0 | Me | Me | CH | 200–201 |
| 3 | Cl | H | 0 | MeO | MeO | CH | 150–151 (decomp.) |
| 4 | —COOMe | H | 0 | Me | Me | CH | 174–175 |
| 5 | —COOMe | H | 0 | Me | MeO | CH | 158–160 |
| 6 | —COOMe | H | 0 | MeO | MeO | CH | 167–168 |
| 7 | —COOMe | H | 0 | MeO | MeO | N | 148 |
| 8 | Me | H | 0 | Me | Me | CH | 210 (decomp.) |
| 9 | Me | H | 0 | Me | MeO | CH | 205–207 |
| 10 | Me | H | 0 | MeO | MeO | CH | 155–156 |
| 11 | Me | 6-Me | 0 | MeO | MeO | CH | 161–162 |
| 12 | —NHCOOEt | H | 0 | Me | Me | CH | 178–179 |
| 13 | —NHCOCOOEt | H | 0 | Me | MeO | CH | 188–190 |
| 14 | —NHCOCH$_2$CH$_2$CH$_2$Cl | H | 0 | Me | MeO | CH | 164–166 |
| 15 | —OCHF$_2$ | H | 0 | MeO | MeO | CH | 176–177 |
| 16 | Cl | H | 1 | Me | Me | CH | 180–181 |
| 17 | Cl | H | 1 | Me | MeO | CH | 176–178 |
| 18 | Cl | H | 1 | MeO | MeO | CH | 150–151 |
| 19 | —COOMe | H | 1 | Me | Me | CH | 163 |
| 20 | —COOMe | H | 1 | Me | MeO | CH | 181–183 |
| 22 | —COOMe | H | 1 | MeO | MeO | N | 163 |
| 23 | —COOMe | 6-NO$_2$ | 1 | MeO | MeO | CH | 174–175 |
| 24 | —CN | H | 1 | Me | Me | CH | 225 (decomp.) |
| 25 | —CN | H | 1 | Me | MeO | CH | 208 |
| 26 | —CN | H | 1 | MeO | MeO | N | 245 (decomp.) |
| 27 | —NO$_2$ | H | 1 | Me | MeO | CH | 239–240 |
| 28 | —NO$_2$ | H | 1 | MeO | MeO | CH | 176–178 |

TABLE 3-continued

General formula $$\text{(structure with } R_A, R_B \text{ on benzene ring, } -(CH_2)_n-SO_2N=C(S-N=C(R_2)-Z=C(R_3)-N) \text{ ring)}$$

| Compd. No. | $R_A$ | $R_B$ | n | $R_2$ | $R_3$ | Z | mp (°C.) |
|---|---|---|---|---|---|---|---|
| 29 | —NO$_2$ | H | 1 | MeO | MeO | N | 158–160 |
| 30 | —SO$_2$Me | H | 1 | MeO | MeO | CH | 180–181 |
| 31 | —SO$_2$NMe$_2$ | H | 1 | MeO | MeO | CH | 159–161 |
| 34 | COOMe | H | 0 | Me | MeO | N | 158–159 (decomp.) |

Formulation Example 4

Emulsifiable concentrates, containing:

| | |
|---|---|
| Compound No. 4 | 2% |
| xylene | 75% |
| dimethylformamide | 18% |
| polyethylene glycol ether (Nonipol 85 ®) | 5% |

(to be used suitably with dilution in water)

Formulation Example 2

Wettable powders, as prepared by blending and grinding the following components:

| | |
|---|---|
| Compound No. 10 | 30% |
| sodium ligninsulfonate | 5% |
| polyoxyethylene glycol ether (Nonipol 85 ®) | 5% |
| clay | 55% |
| white carbon | 5% |

(to be used suitably with dilution in water)

Formulation Example 3

Granules, as prepared by adding water to the following mixture, blending and granulating:

| | |
|---|---|
| Compound No. 21 | 0.5% |
| sodium ligninsulfonate | 2% |
| bentonite | 57.5% |
| talc | 40% |

Formulation Example 4

Granules, as prepared by adding water to the following mixture, blending and granulating:

| | |
|---|---|
| Compound No. 20 | 1% |
| sodium ligninsulfonate | 5% |
| bentonite | 94% |

Test Example 1 (Herbicidal test)

Paddy soil was put in a square-shaped plastic pot having a surface area of 150 cm$^2$. After introducing water and scratching the bed, seeds of *Echinochloa oryzicola*, *Cyperus difformis*, *Scirpus juncoides*, *Lindernia procumbens* and *Rotala indica* were sowed, and further tubers of *Sagittaria Pygmaea* were planted. Cultivation was effected for a prescribed term, while filling the pot with water up to 3 cm height over the bed surface. When monocotyl weeds grew up to the mono-leaf period a dilute solution containing a test compound was applied into the pot, so that 1 g of the test compound was applied per are of the bed surface. The dilute solution was prepared by dissolving 1 g of the test compound in 200 ml of acetone containing 2%(W/V) of a surface active agent Tween 20 ® and diluting with water up to 40 l in total.

Three weeks after the application, herbicidal effects on each of the test compounds were evaluated according to the following standards (the same standards are used in tests mentioned below):

| Index number | Effect | Control ratio (Herbicidal ratio) % |
|---|---|---|
| 0 | non | 0 |
| 1 | slight | 0.1 to 50 |
| 2 | small | 50.1 to 75 |
| 3 | medium | 75.1 to 87.5 |
| 4 | large | 87.6 to 99.9 |
| 5 | extremely large | 100 |

The results are shown in Table 4.

TABLE 4

| Test Compound (Compound No.) | Herbicidal Effect | | | | | |
|---|---|---|---|---|---|---|
| | A | B | C | D | E | F |
| 1 | 4 | 5 | 4 | 4 | 4 | 4 |
| 2 | 4 | 4 | 4 | 4 | 4 | 4 |
| 4 | 4 | 5 | 5 | 5 | 4 | 4 |
| 5 | 4 | 5 | 5 | 5 | 4 | 4 |
| 6 | 4 | 5 | 5 | 5 | 4 | 4 |
| 7 | 4 | 4 | 4 | 3 | 4 | 4 |
| 10 | 4 | 4 | 4 | 4 | 4 | 4 |
| 20 | 3 | 4 | 3 | 4 | 3 | 3 |
| 21 | 3 | 4 | 4 | 4 | 4 | 4 |
| 30 | 5 | 5 | 3 | 4 | 4 | 4 |
| 31 | 3 | 4 | 3 | 4 | 4 | 4 |
| 32 | 3 | 4 | 3 | 3 | 3 | 4 |

A: *Echinochloa oryzicola*
B: *Cyperus difformis*
C: *Lindernia procumbens*
D: *Rotala indica*
E: *Scirpus juncoides*
F: *Sagittaria pygmaea*

It is clear from the above test results that the compounds (I) of the invention exhibit excellent herbicidal activities.

Test Example 2 (Test for selectivity on rice)

Paddy soil was put in a Wagner pot having a surface area of 1/10000 are, and seeds of *Cyperus difformis, Monochoria vaginalis, Lindernia procumbens* and *Rotala indica* were sowed. After cultivation for one week, two nursery rice-plants were transplanted to the bed. In another pot were sowed seeds of *Echinochloa oryzicola* and *Scirupus juncoides*, and in still another pot was scattered paddy soil containing biennal stems of *Eleocharis acicularis* and, after planting budding tubers of *Sagittaria pygmae*, were planted budding tubers of *Cyperus serotinus* with the buds bared on the surface of the soil. Every pot was filled with water up to 3 cm height over the bed surface. Then, one week after the transplantation of rice-plants (the mono-leaf period of *Echinochloa oryzicola*), a prescribed amount [0.1 g or 2.5 g of the active ingredient of the compound (I), per are] of granules containing 0.2 % of a compound (I), which were prepared in the same manner as Formulation Example 3, was applied to water of each pot. For contrast, 2.5% Simetryn granules were applied in the amount of 5.0 g of the active ingredient, per are and also each granules of compound A and B (as formulated by the same way as in Formulation Example 3) were applied in the amount of 1.0 g of the active ingredient, per are. 21 days after application, herbicidal effects and harmful effects were evaluated on each test compounds.

Besides, harmful effects on rice, barley and wheat are shown by the following index numbers:

| Index number | Harmful Effect | Damage ratio % |
|---|---|---|
| 0 | none | 0 |
| 1 | slight | 0.1 to 12.5 |
| 2 | small | 12.6 to 25 |
| 3 | medium | 25.1 to 50.0 |
| 4 | large | 50.1 to 99.9 |
| 5 | extremely large | 100 |

The results are shown in Table 5

TABLE 5

| Test Compound (Compound No.) | Application rate (g/are) | Harmful Effect rice | Herbicidal Effect |||||||||
|---|---|---|---|---|---|---|---|---|---|---|---|
| | | | A | B | G | C | D | E | H | I | F |
| 20 | 2.5 | 0 | 3 | 3 | 3 | 3 | 4 | 4 | 3 | 3 | 3 |
| 21 | 1.0 | 0 | 3 | 4 | 4 | 4 | 4 | 4 | 3 | 4 | 4 |
| 32 | 1.0 | 0 | 3 | 4 | 4 | 3 | 3 | 3 | 3 | 3 | 4 |
| (For contrast*) Simetryn | 5.0 | 2 | 4 | 4 | 5 | 5 | 5 | 3 | 1 | 2 | 1 |
| Compound A | 1.0 | 4 | 4 | 4 | 3 | 3 | 3 | 4 | 3 | 3 | 4 |
| Compound B | 1.0 | 4 | 4 | 4 | 3 | 1 | 3 | 3 | 3 | 3 | 3 |

A: *Echinochloa oryzicola*
B: *Cyperus difformis*
G: *Monochoria vaginalis*
C: *Lindernia procumbens*
D: *Rotala indica*
E: *Scirpus juncoides*
H: *Cyperus serotinus*
I: *Eleocharis acicularis*
F: *Sagittaria pygmaea*
*Contrast compound
Simetryn:

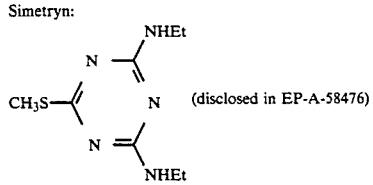

(disclosed in EP-A-58476)

Compound A:

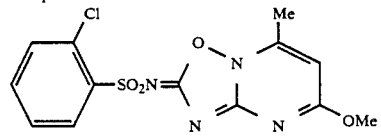

Compound B:

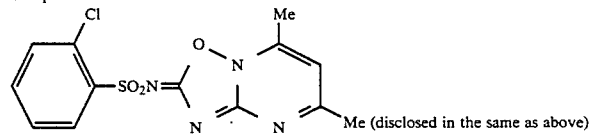

(disclosed in the same as above)

From the above results, it is clear that the compounds (I) of the invention exhibit more excellent selectivity and higher herbicidal activity in comparison with known herbicidal compounds.

Test Example 3 (Test for herbicidal effect)

Sand soil was put in Diffy Pot ® having a diameter of 10 cm. Seeds of *Amaranthus viridis, Chenopodium album, Polygonum longisetum, Portulaca oleracea, Abutilon theophrasti, Ipomoea purpurea, Xanthium strumarium* and *Datura stramonium* were separately sowed to each of the pots. After filling each of the pots with soil up to 0.5 cm height, cultivation was effected for two or three weeks in a green house. When the plants grew up to the 2 or 3 leaf period, a test solution (prepared by dissolving 1 g of the test compound in 500 ml of acetone containing 2% (W/V) of Tween 20 ® and diluting with water up to 5 l in total) was applied in the amount of 1 g of the test compound, per are.

Two weeks after the application, herbicidal effects on each of the test compounds were evaluated.

The results are shown in Table 6

TABLE 6

| Compound No | Herbicidal Effect | | | | | | | |
|---|---|---|---|---|---|---|---|---|
| | J | K | L | M | N | O | P | Q |
| 1 | 4 | 4 | 4 | 4 | 4 | 3 | 3 | 3 |
| 2 | 3 | 3 | 3 | 3 | 3 | 3 | 3 | 3 |
| 4 | 4 | 4 | 4 | 3 | 4 | 4 | 3 | 3 |
| 5 | 4 | 3 | 3 | 3 | 4 | 3 | 3 | 4 |
| 6 | 4 | 4 | 4 | 3 | 4 | 3 | 3 | 3 |
| 7 | 4 | 3 | 3 | 3 | 3 | 3 | 4 | 3 |
| 10 | 3 | 4 | 3 | 3 | 3 | 3 | 3 | 3 |
| 34 | 4 | 4 | 4 | 3 | 4 | 3 | 3 | 3 |

J: *Amaranthus viridis*
K: *Chenopodium album*
L: *Polygonum longisetum*
M: *Portulaca oleracea*
N: *Abutilon theophrasti*
O: *Ipomoea purpurea*
P: *Xanthium strumarium*
Q: *Datura stramonium*

As shown by the above results, it is clear that the compounds (I) of the invention show excellent herbicidal effects.

Test Example 4 (Test for selectivity on barley and wheat)

Sand soil was put in Diffy Pot ® having a diameter of 10 cm. Seeds of *Chenopodium album*, *Brasica* sp, *Stellaria media*, barley and wheat were separately sowed to each of the pots. After filling each of the pots with soil up to 0.5 cm height, cultivation was effected for two or three weeks in a green house. When the plants grew up to the 2 or 3 leaf period, a predetermined amount of a test solution [which is prepared by diluting wettable powders (as shown in Formulation Example 2) with water up to 5 l in total and is used in the amount of 5 l of the test solution, per are] was applied to the stem and leaf by means of a spraygun. Three weeks after the treatment, herbicidal effects and harmful effects were evaluated.

The results are shown in Table 7.

TABLE 7

| Test Compound (Compound No.) | Application rate (g/are) | Herbicidal Effect | | | Harmful Effect | |
|---|---|---|---|---|---|---|
| | | K | R | S | barley | wheat |
| 7 | 0.5 | 3 | 5 | 4 | 0 | 0 |
| | 1.0 | 3 | 5 | 4 | 0 | 0 |
| 10 | 0.5 | 4 | 5 | 4 | 0 | 0 |
| | 1.0 | 4 | 5 | 4 | 0 | 0 |
| 34 | 0.5 | 4 | 5 | 4 | 0 | 0 |
| | 1.0 | 4 | 5 | 4 | 0 | 0 |
| (For contrast) | 0.5 | 3 | 5 | 3 | 3 | 2 |
| Compound A | 1.0 | 4 | 5 | 3 | 4 | 4 |
| Compound B | 0.5 | 3 | 5 | 3 | 1 | 2 |
| | 1.0 | 4 | 5 | 3 | 3 | 3 |

K: *Chenopadium album*
R: *Brasica sp.*
S: *Stellaria media*

It is clear from the above mentioned results that the compounds (I) of the invention are superior in selectivity and exert excellent herbicidal effects, in comparison with known herbicidal compounds.

What is claimed is:

1. A compound of the formula

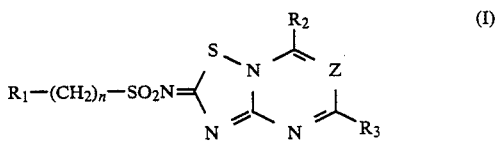

wherein $R_1$ is a phenyl group which is unsubstituted or substituted by one to five substituents selected from the group consisting of lower alkyl, lower alkenyl, lower alkynyl, lower alkoxy, aryl containing 6 to 14 carbon atoms, aryloxy containing 6 to 14 carbon atoms, aralkyl containing 7 to 9 carbon atoms, aralkyoxy containing 7 to 19 carbon atoms, an acyl group selected from the group consisting of lower alkylcarbonyl, lower alkenylcarbonyl, arylcarbonyl, aralkylcarbonyl, lower alkoxycarbonyl, aryloxycarbonyl, aralkyloxycarbonyl, lower alkoxycarbonyl-carbonyl, heterocyclic oxycarbonyl and heterocyclic carbonyl in which all of the aryl and aralkyl moieties have the same meanings as defined above and the heterocyclic moiety is thienyl, benzothienyl, pyrrolyl, oxazolyl, piperazinyl, thiazolyl, thiadiazolyl, pyrazolyl, tetrazolyl or oxazinyl, which acyl group is unsubstituted or substituted by one to three halogen atoms, acyloxy, in which acyl has the same meaning as defined above, acylamino in which acyl has the same meaning as defined above, carbamoyl, thiocarbamoyl, carbamoyloxy, sulfamoyl, sulfamoyloxy, halogen, carboxy, hydroxy, mercapto, lower alkylamino, arylamino in which aryl has the same meaning as defined above, aralkylamino in which aralkyl has the same meaning as defined above, nitro, cyano, and a group of the formula

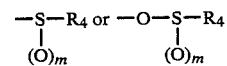

wherein $R_4$ is lower alkyl, lower alkenyl, lower alkoxy, aryl containing 6 to 14 carbon atoms, aryloxy in which aryl has the same meaning as defined above, aralkyl containing 7 to 19 carbon atoms, aralkyloxy containing 7 to 19 carbon atoms, an acyl group selected from the group consisting of lower alkylcarbonyl, lower alkenylcarbonyl, arylcarbonyl, aralkylcarbonyl, lower alkoxycarbonyl, aryloxycarbonyl, aralkyloxycarbonyl, lower alkoxycarbonyl-carbonyl, heterocyclic oxycarbonyl and heterocyclic carbonyl in which all of the aryl and aralkyl moieties have the same meanings as defined above and the heterocyclic moiety is thienyl, benzothienyl, pyrrolyl, oxazolyl, piperazinyl, thiazolyl, thiadiazolyl, pyrazolyl, tetrazolyl or oxazinyl, which acyl group is unsubstituted or substituted by one to three halogen atoms, acyloxy in which acyl has the same meaning as defined above, acylamino in which acyl has the same meaning as defined above, lower alkylamino, arylamino in which aryl has the same meaning as defined above, aralkylamino in which aralkyl has the same meaning as defining above, thienyl, benzothienyl, pyrrolyl, oxazolyl, piperazinyl, thiazolyl, thiadiazolyl, pyrazolyl, tetrazolyl or oxazinyl, and m is 0, 1 or 2, $R_2$ and $R_3$ respectively are a lower alkyl or lower alkoxy group, Z is CH, and n is 0 or 1, or a salt thereof.

2. A compound of claim 1 in which the group $R_1-(CH_2)_n-$ is a group of the formula:

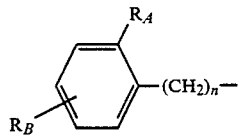

wherein $R_A$ is an acylamino group in which the acyl is selected from the group consisting of lower alkenylcarbonyl, lower alkenylcarbonyl, arylcarbonyl, aralkylcarbonyl, lower alkoxycarbonyl, aryloxycarbonyl, aralkyloxycarbonyl, lower alkoxycarbonyl-carbonyl, heterocyclic oxycarbonyl and heterocyclic carbonyl in which all of the aryl and aralkyl moieties have the same meanings as defined above and the heterocyclic moiety is thienyl, benzothienyl, pyrrolyl, oxazolyl, piperazinyl, thiazolyl, thiaziazolyl, pyrazolyl, tetrazolyl or oxazinyl, which acyl group is unsubstituted or substituted by one to three halogen atoms; a lower alkoxycarbonyl group; a lower alkyl group which is unsubstituted or substituted by one to three halogen atoms; a sulfamoyl group which is unsubstituted or substituted by one or two alkyl groups; a lower alkoxy group which is unsubstituted or substituted by one to three halogen atoms; a cyano group; a halogen; a nitro group; or a lower alkylsulfonyl group; $R_B$ is hydrogen, a lower alkyl group or a nitro group; and n is 0 to 1.

3. A compound of claim 2 in which $R_A$ is a halogen; a lower alkoxycarbonyl group; a lower group; a lower alkoxy group which is unsubstituted or substituted by one to three halogen atoms; a lower alkoxycarbonylamino group; a lower alkylcarbonylamino group which is unsubstituted or substituted by one to three halogen atoms; or a lower alkoxycarbonyl-carbonylamino group; $R_B$ is hydrogen or a lower alkyl group; and n is 0.

4. A compound of claim 3 in which $R_A$ is a halogen; a lower alkoxycarbonyl group; a lower alkyl group which is unsubstituted or substituted by one to three halogen atoms; a lower alkoxy group which is unsubstituted or substituted by one to three halogen atoms; a lower alkylsulfonyl group; a sulfamoyl group which is unsubstituted or substituted by one or two lower alkyl groups; a cyano group; or a nitro group; $R_B$ is hydrogen or a nitro group; and n is 1.

5. A compound of claim 3 in which $R_A$ is a halogen, a lower alkoxycarbonyl group or a lower alkyl group; and $R_B$ is hydrogen.

6. A compound of claim 5 in which $R_A$ is a lower alkoxycarbonyl group or a lower alkyl group.

7. A compound of claim 4 in which $R_A$ is a lower alkoxycarbonyl group and $R_B$ is hydrogen.

8. A compound of claim 1 which is 5,7-dimethoxy-2-[(2-methoxycarbonylbenzyl)sulfonyl]imino-2H-[1,2,4]thiadiazolo [2,3-a]pyrimidine.

9. A compound of claim 1 which is 5-methoxy-7-methyl-2-[(2-methoxycarbonylbenzyl)sulfonyl]imino-2H-[1,2,4]thiadiazolo [2,3-a]pyrimidine.

10. A compound of claim 1 which is 5,7-dimethoxy-2-[(2-trifluoromethylbenzyl)sulfonyl]imino-2H-[1,2,4]thiadiazolo [2,3-a]pyrimidine.

11. A compound of claim 1 which is 5,7-dimethoxy-2-[(2-trifluoromethylbenzyl)sulfonyl]imino-2H-[1,2,4]thiadiazolo[2,3-a]pyrimidine.

12. A method of killing weeds in a paddy field which comprises applying a herbicidally effective amount of the compound (I) as claimed in claim 1 wherein n is 1 or a salt thereof to the paddy field.

13. A method of killing weeds in a field which comprises applying a herbicidally effective amount of the compound (I) as claimed in claim 1 wherein n is 0 or a salt thereof to the field.

14. A herbicidal composition which comprises as an active ingredient a compound or a salt of claim 1, and a carrier therefor suitable for herbicidal use of the composition.

15. A process for producing a compound or salt of claim 1, which comprises contacting a compound of the formula:

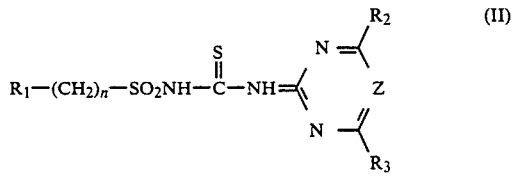

wherein the symbols have the same meanings as defined in claim 1, or a salt thereof, with an oxidizing agent.

* * * * *